(12) United States Patent
Maass et al.

(10) Patent No.: US 9,797,768 B2
(45) Date of Patent: Oct. 24, 2017

(54) LIGHT SENSING DEVICE FOR SENSING AMBIENT LIGHT INTENSITY

(71) Applicant: KONINKLIJKE PHILIPS N.V., Eindhoven (NL)

(72) Inventors: Henning Maass, Waalre (NL); Guido Josef Müsch, Josef (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 6 days.

(21) Appl. No.: 14/648,739

(22) PCT Filed: Nov. 26, 2013

(86) PCT No.: PCT/IB2013/060401
§ 371 (c)(1),
(2) Date: Jun. 1, 2015

(87) PCT Pub. No.: WO2014/097020
PCT Pub. Date: Jun. 26, 2014

(65) Prior Publication Data
US 2015/0300875 A1    Oct. 22, 2015

Related U.S. Application Data

(60) Provisional application No. 61/739,805, filed on Dec. 20, 2012.

(51) Int. Cl.
*G01J 1/44* (2006.01)
*G01J 1/02* (2006.01)
(Continued)

(52) U.S. Cl.
CPC .......... *G01J 1/0228* (2013.01); *A61B 5/4857* (2013.01); *A61B 5/681* (2013.01); *G01J 1/0233* (2013.01);
(Continued)

(58) Field of Classification Search
CPC ..................................................... G10J 1/4204
(Continued)

(56) References Cited

U.S. PATENT DOCUMENTS

2008/0319354 A1    12/2008    Bell et al.
2010/0201275 A1    8/2010    Cok
(Continued)

FOREIGN PATENT DOCUMENTS

CN    1121039 A    4/1996
CN    201043897 Y    4/2008
(Continued)

OTHER PUBLICATIONS

Lockley, S. et al, "Short-Wavelength Sensitivity for the Direct Effects of Light on Alertness, Vigilance, and the Waking Electroencephalogram in Humans", Sleep, vol. 29, No. 2, 2006.
(Continued)

*Primary Examiner* — Thanh Luu
(74) *Attorney, Agent, or Firm* — Michael W. Hass

(57) ABSTRACT

The invention relates to a light sensing device for sensing ambient light intensity, comprising at least one ambient light sensor and an occlusion detector for detecting an object occluding the ambient light sensor. The invention is further related to a corresponding method for sensing ambient light intensity.

14 Claims, 7 Drawing Sheets

(51) Int. Cl.
*A61B 5/00* (2006.01)
*G01J 1/42* (2006.01)
*A61B 5/16* (2006.01)

(52) U.S. Cl.
CPC ............. *G01J 1/4204* (2013.01); *A61B 5/165* (2013.01); *A61B 2560/0242* (2013.01); *A61B 2560/0475* (2013.01); *G01J 2001/0257* (2013.01)

(58) Field of Classification Search
USPC .................................................. 250/214 AL
See application file for complete search history.

(56) References Cited

U.S. PATENT DOCUMENTS

| | | | |
|---|---|---|---|
| 2010/0273530 A1 | 10/2010 | Jarvis et al. | |
| 2012/0132806 A1 | 5/2012 | Findlay et al. | |
| 2012/0162636 A1* | 6/2012 | Sy | G01S 17/026 356/51 |
| 2013/0182246 A1* | 7/2013 | Tanase | G06F 3/042 356/218 |
| 2013/0215007 A1* | 8/2013 | Hung | G06F 1/1677 345/156 |

FOREIGN PATENT DOCUMENTS

| | | |
|---|---|---|
| CN | 102379002 A | 3/2012 |
| EP | 2424201 A2 | 2/2012 |
| WO | WO9608734 A2 | 3/1996 |
| WO | 2004032715 A2 | 4/2004 |

OTHER PUBLICATIONS

Philips Respironics: Twice As Easy—"Ambulatory Actigraphy Devices That Collect and Download Continuous, Objective Long-Term Sleep/Wake Data", Actigraphy Product Brochure, 2012, From http://actiwatch.respironics.com/.

Texas Advanced Optoelectronics Solutions: TCS3772 "Color Light-To-Digital Converter With Proximity Sensing", Apr. 2012.

Terman, M et al, "Light Therapy for Seasonal and Nonseasonal Depression: Efficacy, Protocol, Safety, and Side Effects", CNS Spectrums, Aug. 2005, pp. 647-663.

* cited by examiner

LIGHT SENSING DEVICE FOR SENSING AMBIENT LIGHT INTENSITY

CROSS-REFERENCE TO PRIOR APPLICATIONS

This application is the U.S. National Phase application under 35 U.S.C. §371 of International Application No. PCT/IB2013/060401, filed on Nov. 26, 2013, which claims the benefit of U.S. Provisional Patent Application No. 61/739,805, filed on Dec. 20, 2012. These applications are hereby incorporated by reference herein.

FIELD OF THE INVENTION

The invention relates to the field of wrist-worn devices for sensing ambient light intensity, as well as to a corresponding method for sensing ambient light intensity using such a wrist-worn device.

BACKGROUND OF THE INVENTION

Exposure to light is the key mechanism that enables a proper synchronization of the body clock with the solar day cycle. Timing, duration, intensity and spectral composition of light exposure all have impact on the so-called entrainment of a person to a 24-hour circadian rhythm. It has been shown that restorative sleep can only occur in synchronicity with the body clock. For certain people who have a phase shift of their internal body clock relative to the social schedules around them, exposure to bright light at well-defined times can be used to shift their body clock forward or backwards to better align it with their social needs. Also for the treatment of seasonal affective disorder, timed and regular exposure to bright light is an effective means.

The assessment of light levels to which a person is exposed over the course of multiple days or even weeks is an important instrument for the diagnosis of mood and sleep disorders. Existing actigraphy products measure the activity and light exposure with a body-worn device, for example, a wrist-worn device that is used and worn similar to a wristwatch.

Such a wrist-worn device is shown, for example, in US 2008/0319354 A1, showing a system and method for monitoring information related to sleep. The wrist-worn device shown in this document comprises an illumination sensor to provide an information related to the intensity of ambient illumination of the user. The signal of the sensor can be further processed by suitable electronic computing means.

A problem related to the common body worn devices, such as wrist-worn devices, is to detect the presence of an object occluding the light sensor. Such an occlusion may falsify the exposure measurement of ambient light to the user. A typical example for an occluding object is a sleeve of the user's clothing that covers an ambient light sensor integrated into a wrist-worn light sensing device. With the present light sensing devices, it is impossible to determine whether or not the ambient light sensor is occluded by any object, although this information would facilitate the analysis of the exposure data. For example, it would be possible to exclude occlusion periods from the analysis completely. Moreover, it is desired to inform the user of the light sensing device about the occluded state, so he can take counter measures to remove the occluding object from the light sensor to expose it to the ambient light again.

SUMMARY OF THE INVENTION

It is therefore an object of the present invention to provide a light sensing device for sensing ambient light intensity that allows the detection of an object occluding the light sensor for improving the overall reliability of exposure data gained by the ambient light sensor, also providing the option to inform a user about an occluded state of the light sensor to take counter measures against the occlusion.

This object is achieved by a light sensing device comprising the features of claim 1.

The light sensing device according to the present invention comprises an occlusion detector for detecting an object occluding the ambient light sensor. This detection gives an additional information that can be used to analyse the exposure situation accordingly, providing an occlusion status information allocated to the ambient light intensity measured by the light sensor, and to inform the user about the occluded state so that he can remove the occluding object. This improves the overall reliability of the gained intensity data. The occlusion status information can also be stored together with the intensity measurements to enhance post processing of the exposure information, e.g. by filling measurement gaps.

The occlusion detector can be of any kind to detect the presence of the occluding object, for example, a proximity sensor that detects the presence of an object in the near environment of the ambient light sensor.

According to a preferred embodiment of the present invention, the occlusion detector comprises an infrared sensor and an infrared light source. Such a light source can be, for example, an infrared light emitting device (LED) that emits radiation in the infrared range of the light spectrum. Infrared light reflected by a nearby object is detected by the infrared sensor.

Preferably the light sensing device according to the present invention comprises a casing on which the infrared sensor, the infrared light source and the ambient light sensor are positioned on the same side. By such an arrangement, the infrared light source is able to detect the presence of an object near the side of the casing on which the ambient light sensor is positioned.

Preferably the light sensing device according to the present invention is a wrist wearable device comprising a wristband.

More preferably, the light sensing device according to the present invention further comprises an indicator device for generating an audible, visual and/or haptically perceivable notification signal in case of the detection of an object by the occlusion detector. This notification signal can be interpreted as an alarm perceivable by the user so he can uncover the ambient light sensor by removing the occluding object.

According to another preferred embodiment of the present invention the light sensing device further comprises a processor for processing signals generated by the ambient light sensor and for controlling the occlusion detector, and a memory for storing ambient light values representing the ambient light intensity measured by the ambient light sensor and an occlusion status information representing an occlusion status of the ambient light sensor. These data can be allocated to each other in the memory, i.e., the ambient light values are stored together with allocated occlusion status information for further procession and judgement. The control of the occlusion detector may comprise the activation of the infrared light source and/or of the infrared sensor, and their deactivation.

More preferably, the processor is provided to activate the occlusion detector only in case the ambient light intensity measured by the ambient light sensor is below a predetermined threshold. In this case it is possible that the infrared light source is not activated all the time, saving energy to prolong the operation period of the light sensing device.

The present invention is further related to a method for sensing ambient light intensity by means of a light sensing device comprising at least one ambient light sensor and an occlusion detector for detecting an object occluding the ambient light sensor, comprising the steps of performing an ambient light measurement by means of an ambient light sensor, and performing an occlusion measurement by means of an occlusion detector to determine if the ambient light sensor is occluded by an object.

According to a preferred embodiment of this method, the ambient light measurement is performed within temporally limited subsequent epochs.

More preferably, an occlusion measurement is performed for each epoch. In this case each epoch can be allocated to an information representing the occlusion status, i.e. whether or not the ambient light sensor was occluded during this epoch, so the ambient light values of this epoch can be analysed accordingly.

According to another embodiment of this method, an occlusion measurement is performed only for epochs in which the ambient light intensity is below a predetermined threshold. In this case the occlusion detector is activated only if the ambient light intensity is low, saving energy for operating the light sensing device.

According to another preferred embodiment, an occlusion measurement is performed only for the first epoch in which the ambient light intensity is below a predetermined threshold. If an occluding object is detected, the corresponding epoch is marked as begin of an occlusion in the memory of the device. The advantage of this embodiment is that the occlusion measurement is performed much less often than in cases in which the occlusion measurement is performed for each epoch in which the ambient light intensity is low. Optionally an alarm can be generated in case an epoch is marked as the beginning of an occlusion.

According to another preferred embodiment, an occlusion measurement is performed for the first epoch in which the ambient light intensity is below a predetermined threshold and repeated periodically as long as the ambient light intensity stays below this threshold. In this case additional occlusion measurements are periodically performed after the beginning of an occlusion was detected. With this embodiment the further duration of an occlusion can be detected under dark ambient light conditions. Optionally, when the end of an occlusion is detected, the corresponding measurement epoch is marked as the end of an occlusion. This embodiment allows balancing between energy spent for an occlusion measurement and the accuracy of the occlusion detection.

Also in this embodiment, it is an option to generate an alarm to the user of the device whenever an epoch is determined as the first epoch with an occlusion, i.e. being marked as a beginning of an occlusion. It is further possible to generate alarms not for every occlusion detection but after a predefined time to customize the frequency of alarms to the needs of the user and the application.

According to still another embodiment of this method, an occlusion measurement is performed once or periodically repeated after the ambient light intensity has stayed below a predetermined threshold for a predetermined number of epochs. In this case the occlusion measurement is not performed immediately for the first epoch in which the ambient light level is below the threshold. Instead, it is done if the light level stays below the threshold for a predefined number of epochs. This can be used to avoid the generation of an alarm to the user even for very brief occlusion periods that do not have a major influence on the accuracy of the overall measurement.

According to another preferred embodiment of this method, the predetermined threshold of ambient light intensity and/or a repetition period of occlusion measurements are adjustable by a user.

It is further an option to adapt the predetermined threshold of ambient light intensity and/or the repetition period of occlusion measurements to the date and time of day.

If the ambient light sensor measures low ambient light values in the middle of the day, an occlusion is much more likely than if it senses low light values in the middle of the night during summer or in the late afternoon during winter.

The choice of strategy and the parameters, like threshold of ambient light intensity and number of epochs between proximity sensing, are user programmable in addition to being controlled by date and time of day to adapt the sensing strategy to the application needs.

The present invention is applicable to wrist-worn devices with a wristband but also to other body-worn light sensing devices for detecting an object, like a piece of clothing, occluding the ambient light sensor.

BRIEF DESCRIPTION OF THE DRAWINGS

These and other aspects of the invention will be apparent from and elucidated with reference to the embodiments described hereinafter.

In the drawings.

DETAILED DESCRIPTION OF EMBODIMENTS

Figure 1:
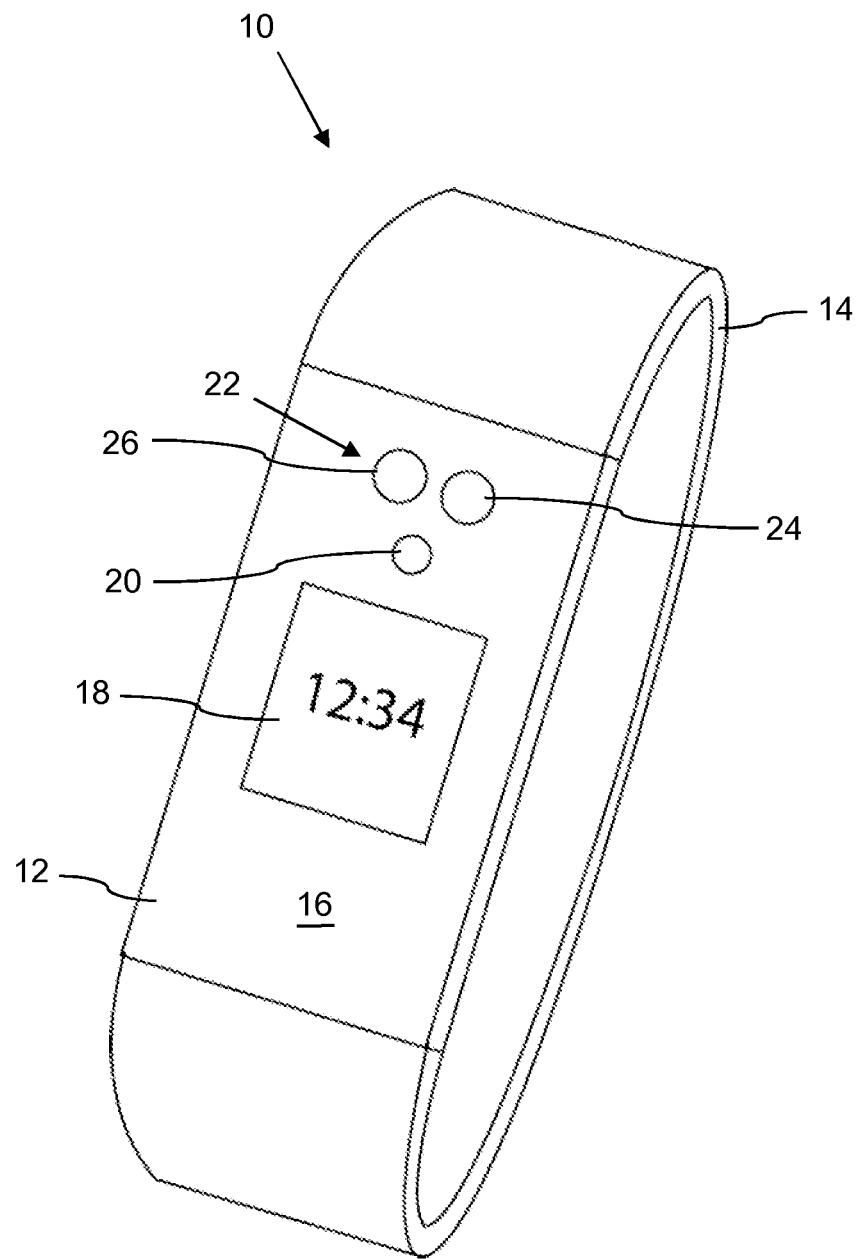
FIG. 1 is a perspective front view of one embodiment of a wrist-worn device according to the present invention.

FIG. 1 shows a light sensing device 10 in the form of a wrist-worn device for sensing the ambient light intensity in the environment of a user (not shown) wearing this device 10. Generally the light sensing device 10 comprises an operation module 12 in the shape of a flat rectangular box, and a flexible wrist band 14 that is attached with its ends to opposite sides of the operation module 12 such that the operation module 12 and the wrist band 14 form a ring. The inner diameter of the wrist band 14 is dimensioned such that the wrist-worn device 10 can comfortably be worn on the wrist of a user. For putting on the device 10, the wrist band 14 may have a certain elasticity to be widened, or an opening and closing mechanism (not shown in the Figures) may be provided for connecting one end of the wrist band 14 to the operation module 12. Generally the operation module 12 and the wrist band 14 are formed similar to a common wrist watch.

The operation module 12 is formed as a housing that receives integrated electronic circuits for processing and storing electric signals and for performing the operation of sensing ambient light intensity, as will be described further below. On the top surface 16 of the operation module 12, there is a display 18 for displaying a status information of the device 10 or any other information, like, for example, the daytime.

Further provided on the top surface 16 of the operation module 12 there is an ambient light sensor 20 for measuring the ambient light intensity. This ambient light sensor 20 is provided to measure the intensity of light within the visible light spectrum and to generate electric signals representing the measured light intensity within this spectrum. These signals can be interpreted as data concerning the present ambient light intensity.

The ambient light sensor 20 can measure one or multiple spectra of interest.

Next to the ambient light sensor 20, an occlusion detector 22 is provided for detecting an object occluding the ambient light sensor 20. This occlusion detector 22 comprises a radiation sensor, namely an infrared (IR) sensor 24 and a radiation light source, namely an infrared (IR) light source 26. This infrared light source 26 can, for example, be an infrared light emitting device (LED) to emit infrared light. This infrared light reflected or scattered by an object or obstacle in front of the ambient light sensor 20 can be detected by the infrared sensor 24 to be interpreted as an occlusion situation in which an object in front of the ambient light sensor 20 occludes this ambient light sensor 20.

Figure 2:
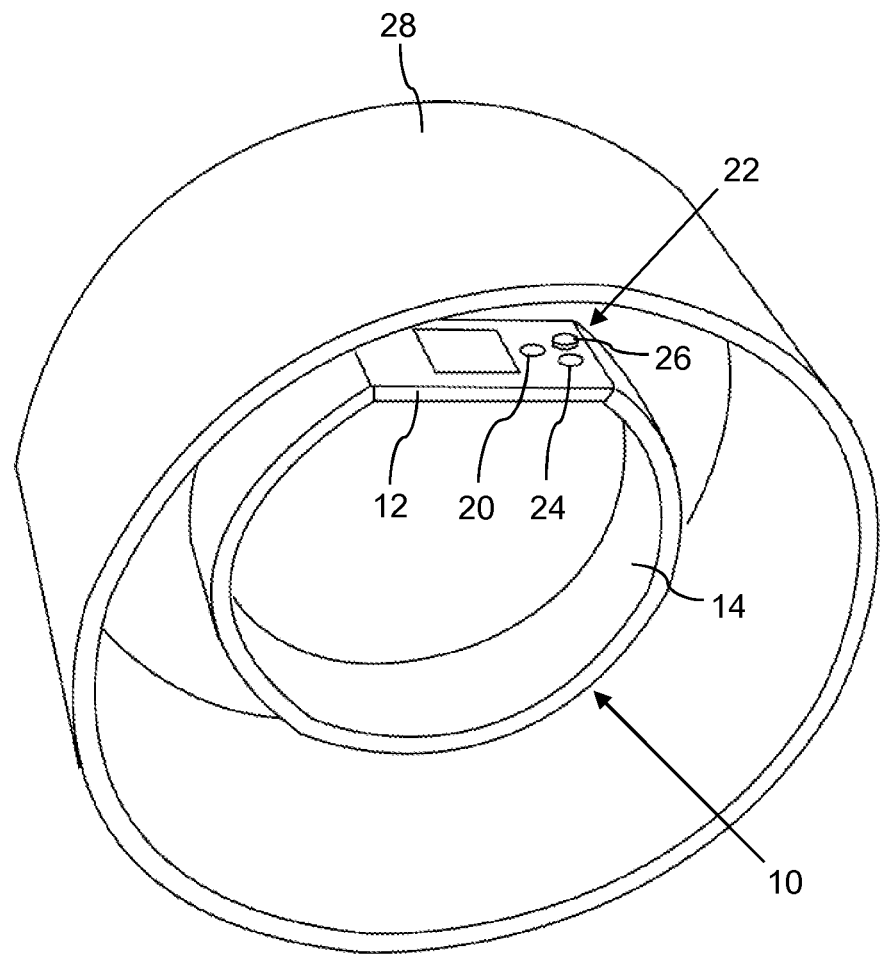
FIG. 2 is a schematic perspective view of the wrist-worn device shown in FIG. 1, covered by a piece of clothing.

Such a situation is shown in FIG. 2. In this situation the wrist-worn light sensing device 10 is surrounded and covered completely by a portion of a sleeve 28 that prevents ambient light to fall on the ambient light sensor 20. This sleeve 28 represents an object occluding the ambient light sensor 20. This object is detected by the occlusion detector 22 as follows. Infrared light radiation emitted by the infrared light source 26 is reflected by the inner surface of the sleeve 28 back to be received by the infrared sensor 24. Upon detection of reflected infrared radiation, the infrared sensor 24 generates a corresponding occlusion status signal that can be further processed by the electronic components of the light sensing device 10. In particular the occlusion status information can be allocated to the data representing the ambient light intensity measured by the ambient light sensor 20.

Figure 3:
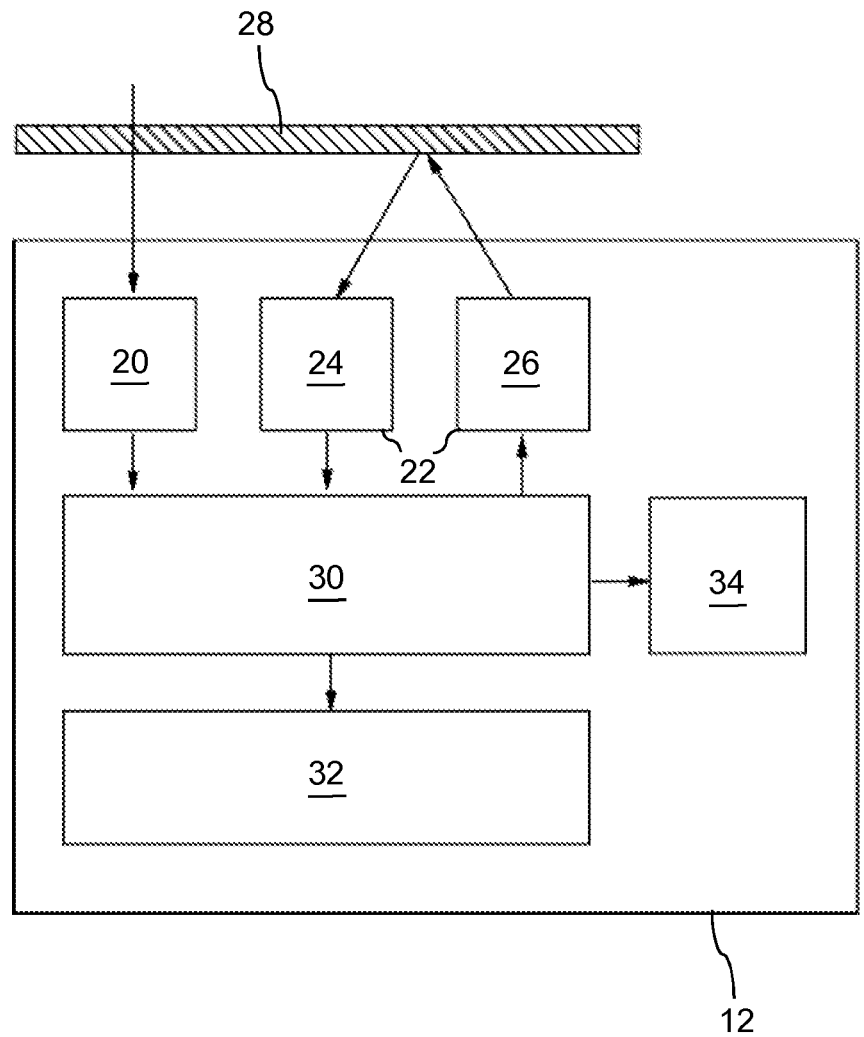
FIG. 3 is a schematic view of the functional components of the light sensing device of FIG. 1.

The schematic view in FIG. 3 shows different components of the light sensing device 10 as explained above. Within the operation module 12, a processor 30 and a memory 32 are provided. It is noted that the terms "processor" and "memory" are only general terms describing electronic devices or circuits that can comprise different electronic devices for performing a processing or storing operation. For example, the processor 30 can comprise one or more electronic circuits for processing signals and for communicating with the ambient light sensor 20, the infrared light sensor 24 and the infrared light source 26 provided on top the operation module 12 and for performing input and output operations with the memory 32.

Signals generated by the ambient light sensor 20 are transmitted to the processor 30 for processing these signals. Moreover, the processor 30 is provided for controlling the occlusion detector 22, in particular for activating and deactivating the infrared light source 26, and for processing signals generated by the infrared sensor 24. The memory 32 is provided for storing ambient light values representing the ambient light intensity measured by the ambient light sensor 20 and an occlusion status information representing an occlusion status of the ambient light sensor 20. For example, ambient light values that are measured when an occlusion is detected by the occlusion detector 22 (i.e. a corresponding signal is generated by the infrared sensor 24) can be marked accordingly in the memory 32.

In particular, the processor 30 is provided to activate the occlusion detector 22 only in case the ambient light intensity measured by the ambient light sensor 20 is below a predetermined threshold. This saves energy for operating the occlusion detector 22, especially the infrared light source 26. It is further possible to process and to store ambient light values within subsequent temporally limited epochs which are limited time periods for performing an ambient light intensity measurement, and to store the ambient light values accordingly. An occlusion status information related to the measurement epoch and representing an occlusion status of the ambient light sensor 20 can also be stored within the memory 32.

The light sensing device 10 further comprises an indicator device 34 for generating an audible, visual and/or haptically perceivable notification signal in case of the detection of an object by the occlusion detector 22. This indicator device 34 is also operated by the processor 30, as shown in FIG. 3, to generate an alarm that can be perceived by the user in case of an occlusion, so the user can remove the occluding object.

In the following different modes of operating the light sensing device 10 as described above will be described in detail. It is noted that in the following description of operations by means of flowcharts, similar processing steps are marked by the same reference numbers, although they are performed in different flows of operation and having a different meaning in the context of each embodiment of the method for sensing ambient light intensity according to the present invention.

Figure 4:
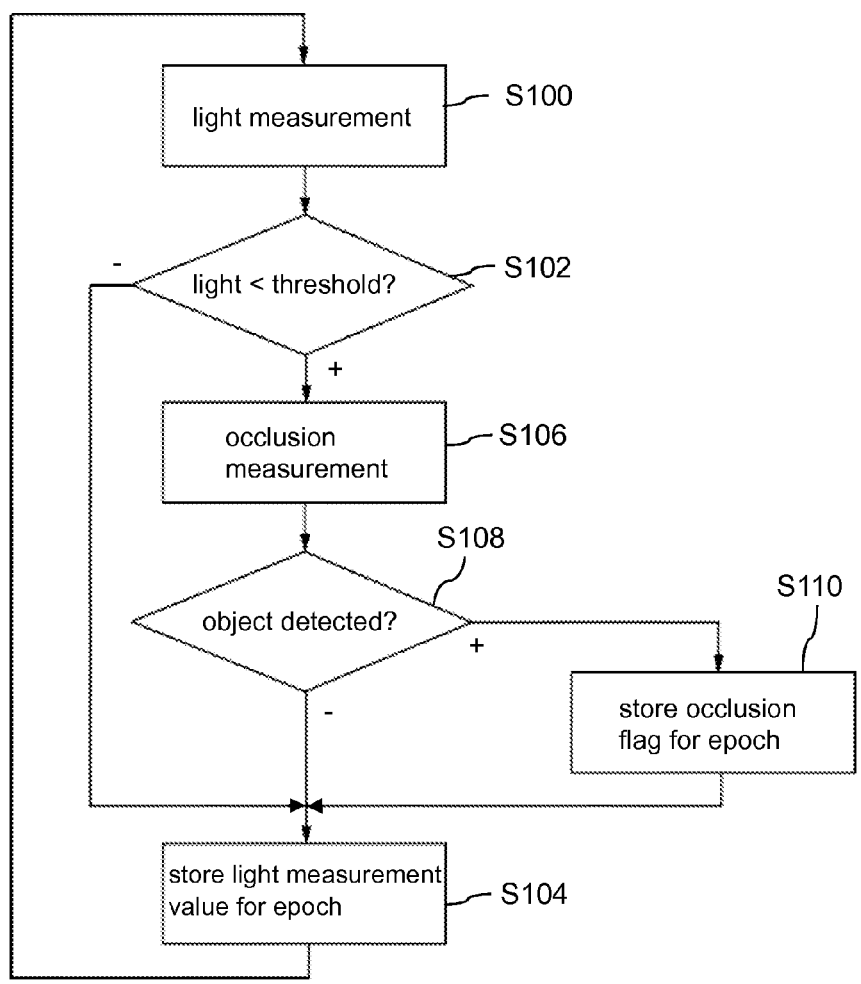
FIGS. 4 to 7 are flow diagrams showing different embodiments of modes of operation of the light sensing device of FIG. 1, representing different embodiments for methods for sensing ambient light intensity.

The flowchart in FIG. 4 represents a basic occlusion sensing operation principle. In step S100, an ambient light measurement is performed by the ambient light sensor 20. In step S102, it is decided whether the ambient light measured in the preceding step S100 is below a predetermined threshold or not. If this is not the case, the operation proceeds with storing the measured ambient light value representing the ambient light intensity in step S104. Afterwards the operation proceeds again with step S100 for taking a further ambient light measurement, as described above.

However, if the decision in step 102 is positive, i.e. it is decided that the ambient light measured in step S100 is below the predetermined threshold, the operation proceeds with an occlusion measurement in step S106 by means of the occlusion detector 22 to determine if the ambient light sensor 20 is occluded by an object. This means that the occlusion measurement in step S106 is performed only in case the light is below the predetermined threshold, and no occlusion measurement is performed when the light is brighter than the predetermined threshold.

After the occlusion measurement in step 106, it is decided whether an object has been detected or not (step S108). If the answer is positive, i.e. an object has been detected, an occlusion flag is set and stored in the memory in step S110, the occlusion flag being related to the present measurement epoch. After step S110, the operation proceeds with step S104 (storing the ambient light value) as described above.

In the above operation, every measurement epoch for which an occlusion has been detected as marked as being occluded in the memory 32 of the light sensing device 10. Alternatively, the information is encoded by storing the epoch numbers for start and end of occlusion.

Figure 5:
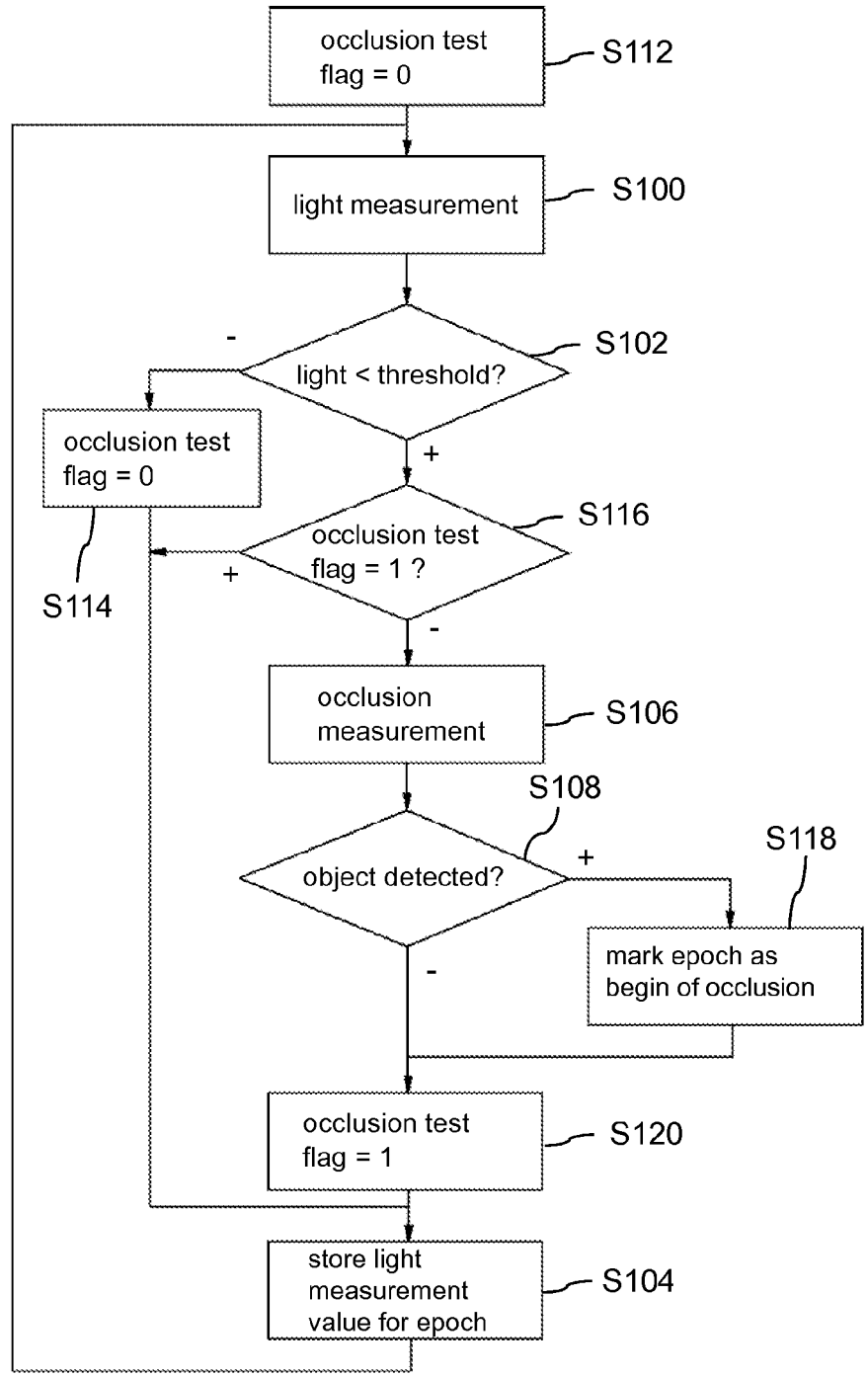

FIG. 5 represents a flowchart showing an operation in which an occlusion measurement is only performed for the first epoch in which the measured ambient light level is below the predetermined threshold.

At the beginning of operation, in step S112, an occlusion test flag is set to the value 0 (zero). Afterwards the operation proceeds with the above described step S100 (sensing ambient light by means of ambient light sensor 20), and with the subsequent step S102 (decision whether the measured ambient light is below the predetermined threshold). If this is not the case, the operation proceeds with a step S114 in which the occlusion test flag is set to 0 (zero), further proceeding with step S104 as described in connection with FIG. 4 (storing the ambient light value for this epoch). After step S104, the operation jumps back to step S100 with another ambient light measurement.

If the decision whether or not the light is below the predetermined threshold in step S102 is positive, the operation proceeds with a step S116, in which it is decided whether the occlusion test flag is set to the value 1. If this is the case, the operation after step S116 further proceeds directly with the above mentioned step S104 (storing ambient light value). However, if the decision in step 116 is negative, i.e. the occlusion test flag is not 1, an occlusion measurement is performed in step S106, like described in FIG. 4, by means of the occlusion detector 22. It is then decided in step S108 whether an object has been detected in the preceding step S106 or not. If the answer is yes, the present epoch is marked as the beginning of an occlusion (S118). Afterwards, in step S120, the occlusion test flag is set to 1, and step S104 is performed.

If the answer in step S108 is negative, i.e. no object has been detected, the operation directly proceeds with step S120 (setting occlusion test flag to 1), and so forth.

This alternative occlusion sensing operation described above in connection with FIG. 5 can be understood as an enlarged version of the operation principle described in connection with FIG. 4, with the difference that the occlusion measurement (step S106) is performed only in case the occlusion text flag has not been set to 1, which is the case in step S120 after each occlusion measurement. This means that in a situation when the light is below the predetermined threshold (decision in step S102) and the occlusion test flag has been set to 1 in a preceding occlusion measurement, no further occlusion measurement is carried out, and the program jumps directly to the storing of ambient light values of the present epoch without performing an occlusion measurement. In the result, an occlusion measurement is performed only in the first epoch in which the ambient light level is below the threshold. If an occluding object is detected, the corresponding epoch is marked as begin of an occlusion in the memory 32 of the device. The advantage of this embodiment of operation is that the occlusion measurement is performed much less often than in the operation flow diagram in FIG. 4. Optionally, in step S118, it is possible to generate an alarm to the user, i.e. a notification signal whenever an epoch is marked as beginning of an occlusion.

Figure 6:
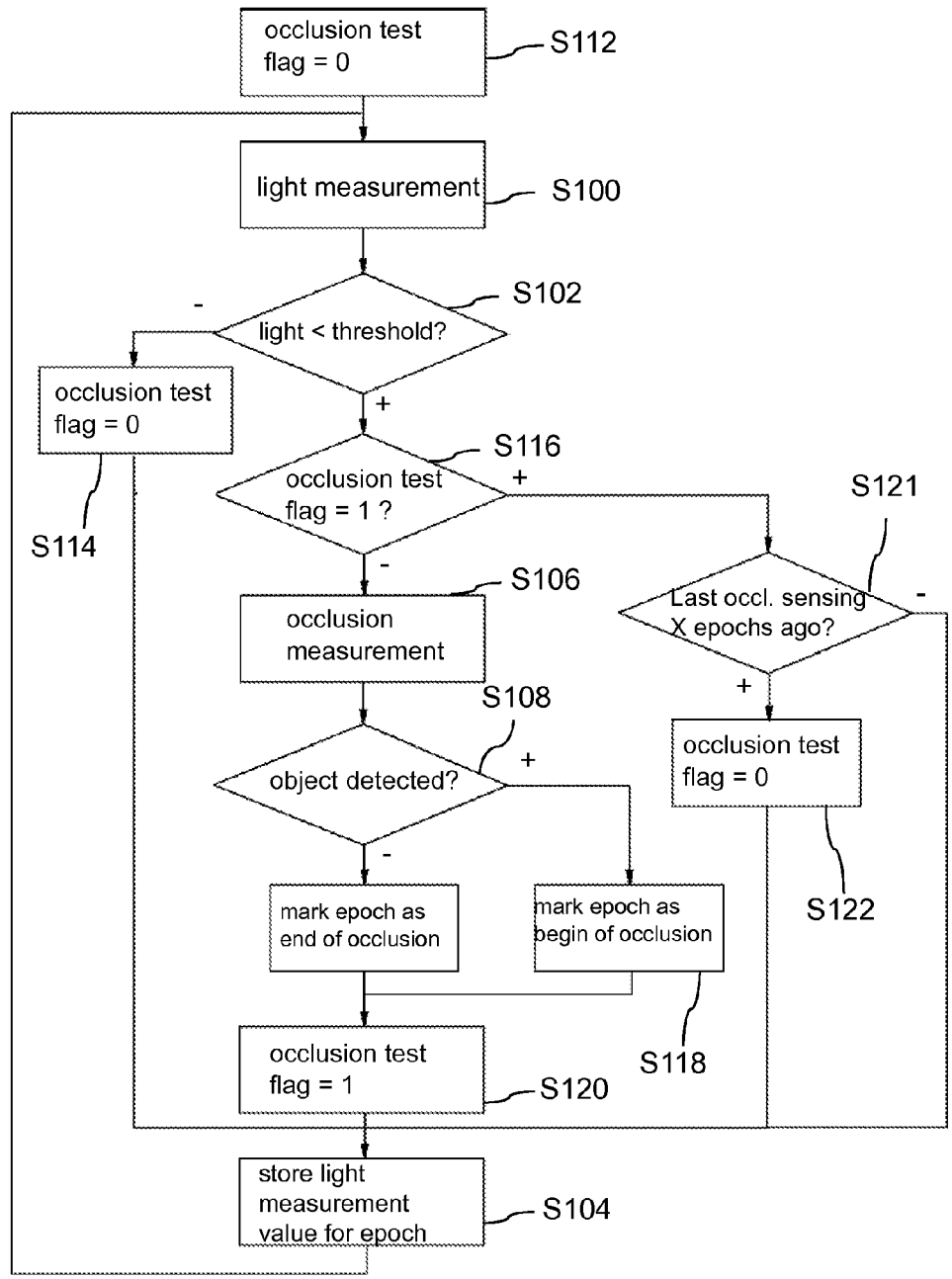

The flow diagram in FIG. 6 demonstrates another occlusion sensing operation principle. FIG. 6 comprises the steps S112 (setting the occlusion test flag to 0 at the beginning of operation), S100 (sensing of ambient light), S102 (deciding whether or not the measured ambient light is below the predetermined threshold), S116 (deciding whether the occlusion test flag is set to 1), S106 (occlusion measurement), S108 (deciding whether an object has been detected or not in the preceding occlusion measurement), S118 (marking a corresponding epoch as beginning of occlusion in case an object has been detected in S108), S120 (setting the occlusion test flag to 1 after the occlusion measurement), S104 (storing ambient light value for epoch), and S114, setting the occlusion test flag to 0 in case the decision in S102 is negative (i.e. the light is not below the predetermined threshold. The sequence of these steps is also the same as described with respect to FIG. 5. Also in FIG. 6, if the light is below the predetermined threshold (S102) and the occlusion test flag is still not set to 1 (S116), an occlusion measurement is performed in step 106. Once the occlusion measurement has been performed, the occlusion test flag is set to 1 in S120, with the consequence that for the time being, no further occlusion measurements will be performed after the subsequent ambient light measurements in step S100.

The difference to the operation according to FIG. 5 lies in that after it has been decided in step S116 that the occlusion test flag is set to 1, it is checked in a following step S121 whether the last occlusion measurement is X epochs ago, while X is a predetermined value. If this is not the case, the operation proceeds with step S104, storing the ambient light value for the present epoch, like in FIG. 5. However, if this decision in step 121 is positive, i.e. the number of epochs has reached the value X, the occlusion test flag is set to Zero again in step S122, preceding further with step S104. As a consequence, in the next operation, another occlusion measurement will be performed in step S106.

In the operation according to FIG. 6, the occlusion measurement in step S106 will be repeated periodically with the period of the value X. The occlusion measurement will be repeated periodically as long as the ambient light intensity stays below the predetermined threshold. This embodiment allows balancing between energy spent for occlusion measurements and accuracy of occlusion detection. With this mechanism also the end of an occlusion period can be detected under dark ambient light conditions, i.e. in situations where the ambient light sensor 20 still measures light levels below the threshold.

According to alternative embodiments of the method for sensing ambient light intensity, an occlusion measurement is performed not immediately for the first epoch in which the light level is below the predetermined threshold. Instead, it is done if the light level stays below the threshold for a predefined number of epochs as shown in the flowchart in FIG. 7. This can be of advantage in combination with generating user alarms to avoid that the user is alarmed for even very brief occlusion periods lasting a single epoch.

Figure 7:
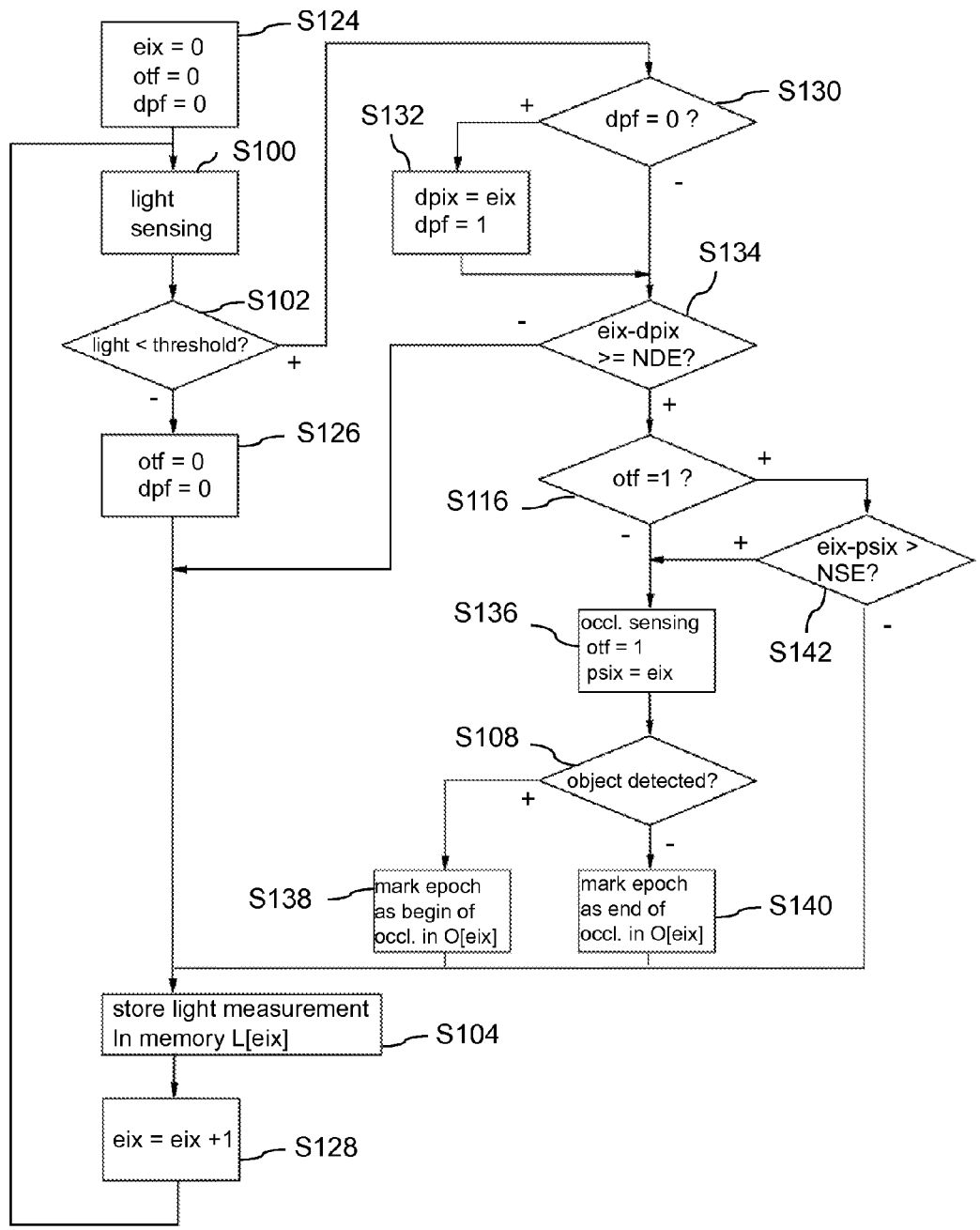

In FIG. 7, a number of parameters are used according to abbreviations as explained below.

otf=occlusion test flag
dpf=dark period flag
eix=epoch index
psix=proximity sensing index
dpix=dark period begin index
L[n]=light value of epoch number n
O[n]=marker for begin or end of occlusion in epoch number n
NDE=number of dark epochs before proximity detection starts
NSE=number of epochs between periodic proximity sensing At the very beginning of the operation, all parameters eix, otf and dpf are set to Zero (that is, the epoch index, the occlusion test flag and the dark period flag), in step S124. Afterwards, an ambient light measurement is performed in step S100, as in the embodiments described above. In step S102, it is decided whether or not the light measured in the preceding ambient light measurement in S100 is below a predetermined threshold. If the answer is negative, the light is equal or above the threshold, it is provided that the occlusion test flag and the dark period flag are both set to Zero in step S126. The light intensity measured in step S100 is stored in step S104, namely as a value L[eix]. After storing, the epoch index is incremented by one in step S128, and the program jumps back to step S100 for another ambient light intensity measurement. The parameter eix is therefore taken as a counter which is incremented with each epoch.

If in step S102, it is determined that the light is below the predetermined threshold, the operation proceeds with a determination whether the dark period flag is set to Zero at present (step S130). If this is the case, the dark period begin index dpix is set to the present epoch index eix in step S132, and at the same time, the dark period flag is set to the value 1. Afterwards the operation proceeds with step S134, as explained below. If the answer in step S130 is negative, i.e. dpf is not set to Zero, the operation directly proceeds from S130 to S134.

The meaning of the above operation in step 132 is to mark the begin of a dark period by the parameter dpix immediately after it has been determined in step S102 that the light is below the threshold, and the dark period flag is set to the value 1 in this case.

Namely, in the following step S134, it is decided whether a predetermined number of dark epochs has already been passed before the occlusion measurement will start. If the present value of eix subtracted by the dark period begin index dpix is larger or equal to the value NDE, the operation will proceed with the occlusion measurement, as will be explained below. If not, the program will proceed directly from step S134 to the storing of the present light value in step S104, without performing an occlusion measurement. This will provide that the first proximity detection will only be performed after darkness is detected for a defined number of epochs (parameter NDE).

In step S116, it is checked whether the occlusion test flag is set to 1. If this is not the case, the operation proceeds with an occlusion measurement in step S136. In this step, the occlusion test flag is set to 1, and the proximity sensing index is further set to the present value of the epoch index. In the following step S108, it is decided whether an object has been detected in the preceding step S136 or not. If the answer is yes, the present epoch is marked as the beginning of an occlusion in the marker O[eix] in step S138. If the answer in step S108 in no, i.e. no object has been detected, the present epoch is marked as the end of an occlusion in O[eix] in step S140. After step S138 or step S140, alternatively, the program proceeds with the step S104, i.e. storing the present ambient light value of this epoch, as described above.

If, however, the answer in step S116 is positive, i.e. it is determined that the occlusion test flag is set to 1, it is checked in step S142 whether the predetermined number of epochs between periodic proximity sensing, which is the parameter NSE, is already reached again. If eix−psix>NSE, another occlusion measurement is performed by proceeding with step S136, as explained above. If the answer is negative, no occlusion measurement is performed and the operation directly proceeds with step S104.

With the light sensing device according to the present invention, different strategies according to the embodiments of methods described above with respect to FIGS. 4 to 7 can be chosen according to certain preconditions, for example, according to parameters such as the date and the time of day. Moreover, the ambient light threshold and the numbers of epochs between subsequent occlusion measurements can be determined by a program or adjusted by a user. If the ambient light sensor measures low ambient light values in the middle of the day, an occlusion is much more likely than if it senses low light values in the middle of the night during summer or in the late afternoon during winter.

During night time or dark hours in winter, the operation according to the flow chart in FIG. 4 offers the advantage of low energy consumption while detecting occlusion of low ambient light levels might be a smaller problem. However, during bright daytime hours, the alternative operation strategies according to FIGS. 5 and 6 might be more suitable for more accurate sensing of occlusion events masking bright ambient light levels.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A light sensing device for sensing ambient light intensity, the light sensing device comprising:
   at least one ambient light sensor configured to measure ambient light intensity;
   an occlusion detector configured to detect an object occluding the ambient light sensor;
   a recording device configured to store ambient light intensity values measured by the ambient light sensor and corresponding occlusion status of the ambient light sensor as a function of time; and
   a processor configured to:
   determine an ambient light intensity threshold based on one or more parameters, the one or more parameters comprising date and/or time of day;
   activate the occlusion detector to measure a first occlusion measurement based on the determined ambient light intensity threshold; and
   determine timing for subsequent activations of the occlusion detector based on the first occlusion measurement and based on the one or more parameters.

2. The light sensing device of claim 1, wherein the occlusion detector comprises an infrared sensor and an infrared light source.

3. The light sensing device of claim 2, comprising a casing on which the infrared sensor, the infrared light source and the ambient light sensor are positioned on the same side.

4. The light sensing device of claim 1, wherein the light sensing device is a wrist-wearable device comprising a wristband.

5. The light sensing device of claim 1, further comprising an indicator device for generating an audible, visual and/or haptically perceivable notification signal in case of the detection of an object by the occlusion detector.

6. The light sensing device according to claim 1, wherein the processor is configured to activate the occlusion detector responsive to the ambient light intensity being below a predetermined threshold.

7. A method for sensing ambient light intensity by means of a light sensing device comprising at least one ambient light sensor an occlusion detector for detecting an object occluding the ambient light sensor a recording device and a processor, comprising the following steps:
- performing an ambient light intensity measurement with the ambient light sensor;
- determining, with the processor, an ambient light intensity threshold based on one or more parameters, the one or more parameters comprising date and/or time of day;
- activating, with the processor, the occlusion detector based on the determined ambient light intensity threshold;
- performing an occlusion measurement with the occlusion detector to determine if the ambient light sensor is occluded by the object;
- recording, with the recording device, ambient light intensity values measured by the ambient light sensor and corresponding occlusion status of the ambient light sensor; and
- determining, with the processor, timing for subsequent activations of the occlusion detector based on the first occlusion measurement and based on the one or more parameters.

8. The method of claim 7, wherein the ambient light measurement is performed within temporally limited subsequent epochs.

9. The method of claim 8, wherein the occlusion measurement is performed for each epoch.

10. The method according to claim 8, wherein the occlusion measurement is performed only for epochs in which the ambient light intensity is below a predetermined threshold.

11. Method according to claim 8, wherein the occlusion measurement is performed only for the first epoch in which the ambient light intensity is below a predetermined threshold.

12. Method according to claim 8, wherein the occlusion measurement is performed for the first epoch in which the ambient light intensity is below a predetermined threshold and repeated periodically as long as the ambient light intensity stays below this threshold.

13. Method according to claim 8, wherein the occlusion measurement is performed once or periodically repeated after the ambient light intensity has stayed below a predetermined threshold for a predetermined number of epochs.

14. Method according to claim 8, wherein the predetermined threshold of ambient light intensity and/or a repetition period of occlusion measurements are adjustable by a user.

* * * * *